(12) United States Patent
Pirrung

(10) Patent No.: US 9,359,309 B2
(45) Date of Patent: Jun. 7, 2016

(54) SYNTHESIS OF SYRBACTIN PROTEASOME INHIBITORS

(71) Applicant: The Regents of the University of California, Oakland, CA (US)

(72) Inventor: Michael C. Pirrung, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/981,857

(22) Filed: Dec. 28, 2015

(65) Prior Publication Data

US 2016/0108007 A1  Apr. 21, 2016

Related U.S. Application Data

(63) Continuation of application No. 13/513,855, filed as application No. PCT/US2010/058855 on Dec. 3, 2010, now Pat. No. 9,221,772.

(60) Provisional application No. 61/266,478, filed on Dec. 3, 2009.

(51) Int. Cl.
*C07D 273/02* (2006.01)
*C07D 285/00* (2006.01)
*C07D 245/02* (2006.01)

(52) U.S. Cl.
CPC .................................. *C07D 245/02* (2013.01)

(58) Field of Classification Search
CPC ..... C07D 273/02; C07D 285/00; C07D 245/02
See application file for complete search history.

(56) References Cited

U.S. PATENT DOCUMENTS

| 4,742,047 A | 5/1988 | Oka et al. |
| 9,221,772 B2 | 12/2015 | Pirrung |
| 2010/0022767 A1 | 1/2010 | Kaiser et al. |

FOREIGN PATENT DOCUMENTS

WO  2009/065090 A2  5/2009

OTHER PUBLICATIONS

Clerc et al., "Synthetic and structural studies on syringolin A and B reveal critical determinants of selectivity and potency of proteasome inhibition," Proc. Natl. Acad. Sci. USA, Apr. 21, 2009, pp. 6507-6512, vol. 106, No. 16.
Kim, Bum Soo, International Search Report and Written Opinion, PCT/US2010/058855, Korean Intellectual Property Office, Aug. 26, 2011.
Honda, Masashi, International Preliminary Report on Patentability and Written Opinion, International Application No. PCT/US2010/058855,Date of Issuance of Report: Jun. 5, 2012.

*Primary Examiner* — Bruck Kifle
(74) *Attorney, Agent, or Firm* — Joseph R. Baker, Jr.; Gavrilovich, Dodd & Lindsey LLP

(57) ABSTRACT

The disclosure relates generally to methods for the preparation of a family of natural compounds, the syrbactins and their analogs.

12 Claims, 2 Drawing Sheets

SYNTHESIS OF SYRBACTIN PROTEASOME INHIBITORS

RELATED APPLICATIONS

Figure 1:
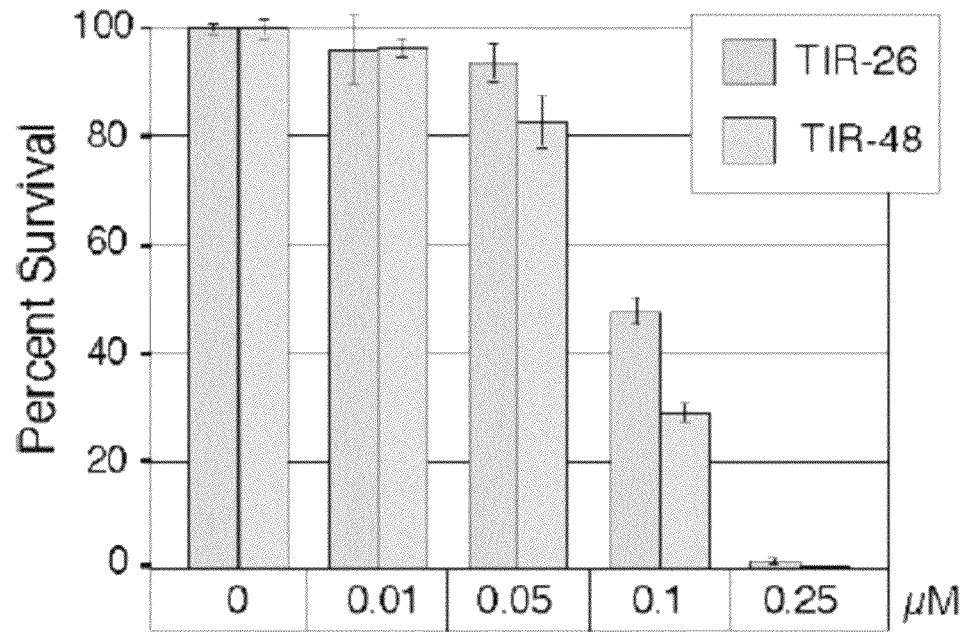

This application is a continuation of U.S. application Ser. No. 13/513,855, now U.S. Pat. No. 9,221,772, filed Nov. 26, 2012, which is a U.S. National Stage Application filed under 35 U.S.C. §371 and claims the benefit of International Application No. PCT/US2010/058855, filed Dec. 3, 2010, which application claims the benefit of priority of provisional application Ser. No. 61/266,478, filed Dec. 3, 2009, the disclosures of which are incorporated herein by reference.

TECHNICAL FIELD

The disclosure relates generally to methods for the preparation of a family of natural compounds, the syrbactins and their analogs.

BACKGROUND

The ability of natural products and other compounds to act as proteasome inhibitors has attracted significant interest because of the wide range of cellular substrates and processes controlled or affected by the ubiquitin-proteasome pathway. For example, the oscillation of cyclins (cell cycle proteins required for the orderly progression through the cell cycle) has been found to be due to the regulated degradation mediated by the ubiquitin-proteasome pathway, and inhibition of this pathway is believed to result in the blockage of cell cycle progression. Additionally, the transcription factor NF-kB is another regulatory protein involved in a variety of cellular processes, including immune and inflammatory responses, apoptosis, and cellular proliferation, whose mode of action is controlled by the ubiquitin-proteasome pathway. Furthermore, it has also been shown that the ubiquitin-proteasome pathway is involved in retrovirus assembly and thus may be a useful target for the development of anti-HIV drugs. For a general discussion of the ubiquitin-proteasome pathway and proteasome inhibitors see, Myung et al. "The Ubiquitin-Proteasome Pathway and Proteasome Inhibitors" Medicinal Research Reviews 2001, 21, 245-273.

SUMMARY

The disclosure provides syrbactin compounds comprising a core ring structure selected from formula I-III:

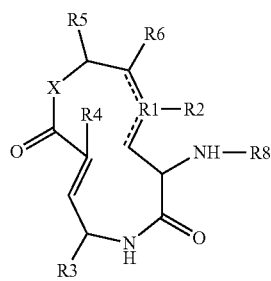

Formula I

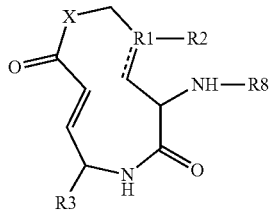

Formula II

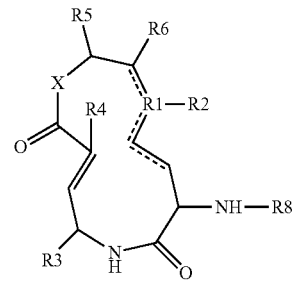

Formula III wherein $R_1$ is selected from O, S or C, wherein $R_2$ is selected from O, H, aryl, substituted aryl, alkyl, substituted alkyl, carboxyl, aminocarbonyl, alkylsulfonylaminocarboxyl, alkoxycarbonyl, and halo, wherein $R_3$ is selected from H, $C(CH_3)_2$, aryl, substituted aryl, alkyl, substituted alkyl, carboxyl, aminocarbonyl, alkylsulfonylaminocarboxyl, alkoxycarbonyl, and halo, wherein $R_4$ is F or H, wherein $R_5$ and $R_6$ are independently H, $OR_7$, or $R_5$ and $R_6$, together with the carbons to which they are bound, can be joined to form a 4 to 7 membered ring or a substituted 4 to 7 membered ring, wherein $R_7$ is selected from H, aryl, substituted aryl, alkyl, substituted alkyl, carboxyl, aminocarbonyl, alkylsulfonylaminocarboxyl, alkoxycarbonyl, and halo, wherein $R_8$ H, an alkyl, a valinyl, or a bis(valinyl) and X is N or O. In one embodiment, $R_8$ comprises the structure:

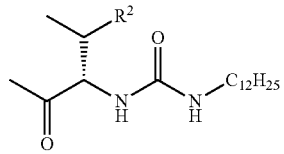

In one embodiment, the core ring structure is selected from formula 11-25:

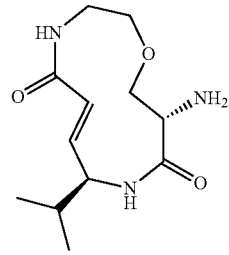

11

12
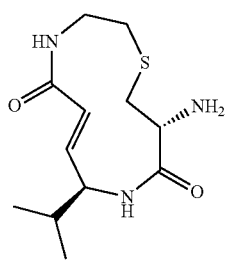
13
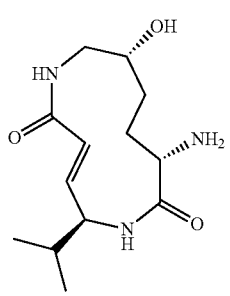
14
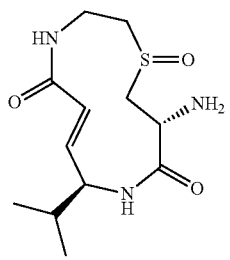
15
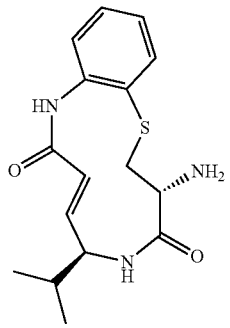
16
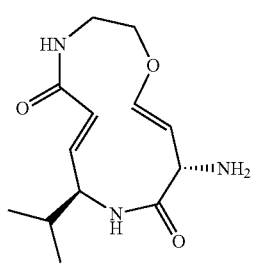
17
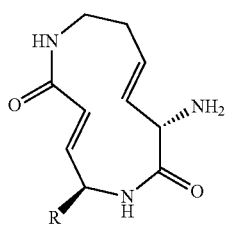
18
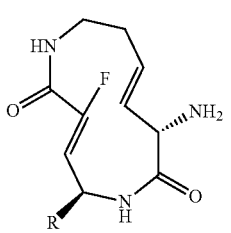
19
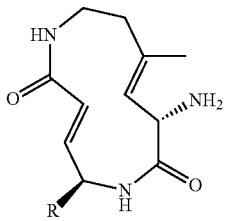
20
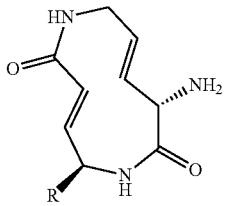
21
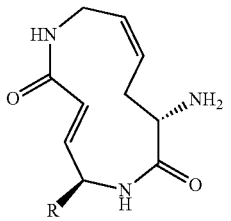
22
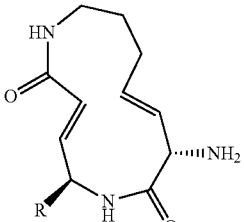
23
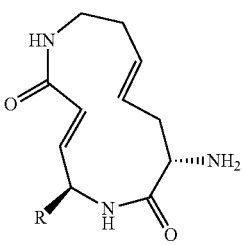

-continued

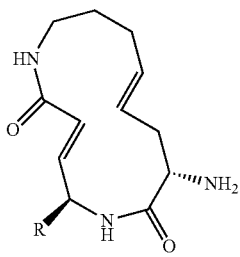

24

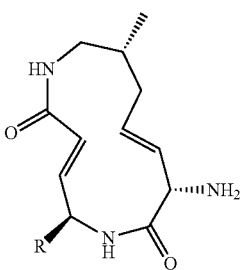

25

In yet another embodiment, the R group of compounds 17-25 is any alkyl or aryl.

The disclosure also provides a composition comprising a syrbactin core structure selected from formula I, II, III, 11-24 or 25 and a pharmaceutically acceptable carrier.

The disclosure also provides a proteasome inhibitor comprising a syrbactin core structure selected from formula I, II, III, 11-24 or 25.

The disclosure provides a method of treating a cancer or inflammatory disease associated with a proteasome comprising contacting a subject having the cancer or inflammatory disease with a compound comprising a syrbactin core structure selected from formula I, II, III, 11-24 or 25.

The disclosure also provides a method of synthesizing a syrbactin, comprising the reaction of scheme I or II, wherein various lysine analogs can be substituted, various oxidation reactions and reagents are substituted, various acylating agents, substituting various amino alcohols in place of valinol.

The disclosure provides a syrbactin compound comprising a core ring structure selected from formula 11-25.

The disclosure also provides a composition comprising syrbactin comprising a core structure selected from formula 11-25 and a pharmaceutically acceptable carrier.

The disclosure provides a proteasome inhibitor comprising a core ring structure selected from formula 11-25.

The disclosure also provides a method of treating a cancer or inflammatory disease associated with a proteasome comprising contacting a subject having the cancer or inflammatory disease with a compound comprising a syrbactin with a core structure selected from formula 11-25.

DETAILED DESCRIPTION OF THE DRAWINGS

FIG. 1 shows the percent survival of acute lymphocytic leukemia cells following contact with TIR26 and TIR48.

Figure 2:
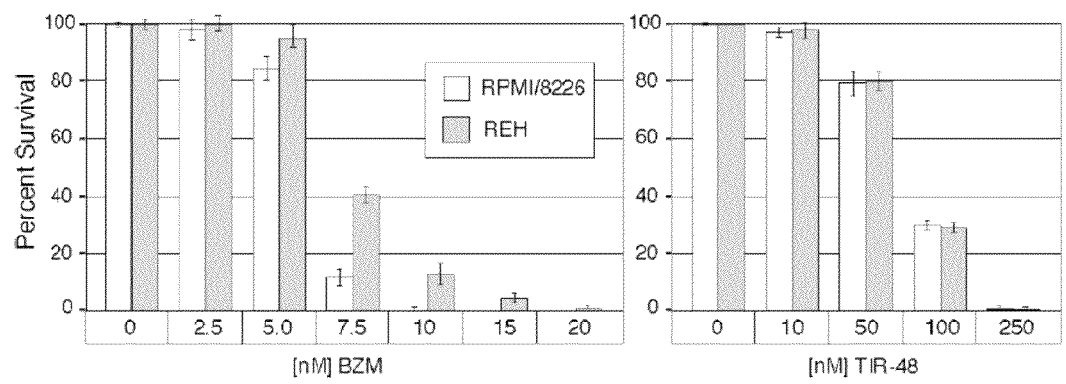

FIG. 2 shows the percent survival of cells following treatment with bortezomib (BZM) or TIR48. The left panel shows that BZM is more cytotoxic to multiple myeloma cells (in this case: the RPMI/8226 cell line) than to acute lymphocytic leukemia cells (in this case: the REH cell line). In comparison, the right panel shows compound TIR-48 is equally effective in both cell lines.

Figure 3:
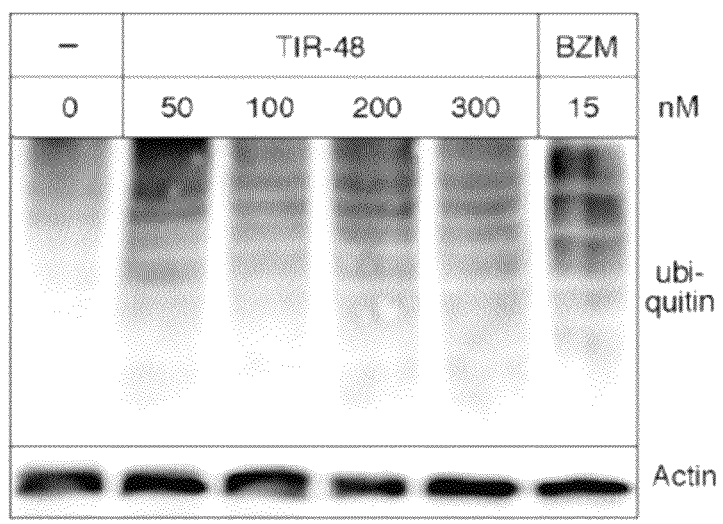

FIG. 3 shows Western blot analysis of REH cells treated with increasing concentrations of TIR-48, and as a positive control, with BZM.

DETAILED DESCRIPTION

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure.

In 2008, two macrolactams, syringolin A and B, were shown to affect plant-pathogen interactions and to act as virulence factors via inhibition of the proteasome. They are members of a bioactive natural product family and includes the glidobactins/cepafungins now referred to as the syrbactins. Crystallography established that both syringolin A and B form a covalent adduct with the proteasome via conjugate addition of the N-terminal threonine hydroxyl group to their α,β-unsaturated lactams. Given the known properties of proteasome inhibitors, the action of syringolin A in cancer cells was investigated. Treatment of a human neuroblastoma cell line with 25 μM syringolin A causes a dose-dependent decrease in proteasome activity and a time-dependent accumulation of ubiquitinated proteins via irreversible inhibition of the proteasome.

As used herein, the term "syrbactin" refers to a novel class of compounds that share a similar chemical core structure and irreversibly inhibiting the catalytic activity of eukaryotic prokaryotic proteasomes. The family of syrbactins includes sub-classifications of molecules called glidobactins, syringolins, and cepafungins. These compounds have utility as anti-cancer agents and as modulators of plant-pathogen interactions. The inhibition of the proteasome has been recognized as a useful property for an anti-cancer agent only over the last decade, with the recent approval of a drug VELCADE (bortezomib) that is currently used to treat refractory multiple myeloma. As bortezomib is a relatively simple synthetic chemical, it may not offer advantages for cancer therapy that have been seen in past natural product anticancer agents. The disclosure provides a large variety of new compositions of matter that readily incorporate structural variations of the core ring structure of the syrbactins, which are almost certain to be components of any marketed drugs to eventually emerge from ongoing research on this family of compounds.

Structures based on the syrbactins would be valuable to access by total synthesis in order to 1) develop novel anticancer therapeutics; 2) better understand plant host-pathogen interactions; and 3) elucidate fundamental questions concerning the structure and function of the proteasome in diverse eukaryotes, including higher plants and even mycobacteria.

used a peptide coupling agent at high dilution to close the macrolactam, which proceeded in 30% yield. Glidobactin A, a natural product with a core closely related to the syringolins, can be synthesized using the techniques disclosed herein. Here, macrolactamization via a pentafluorophenyl active ester gave the 12-membered ring at about 20% yield.

Scheme 1: Synthesis of Syringolin B

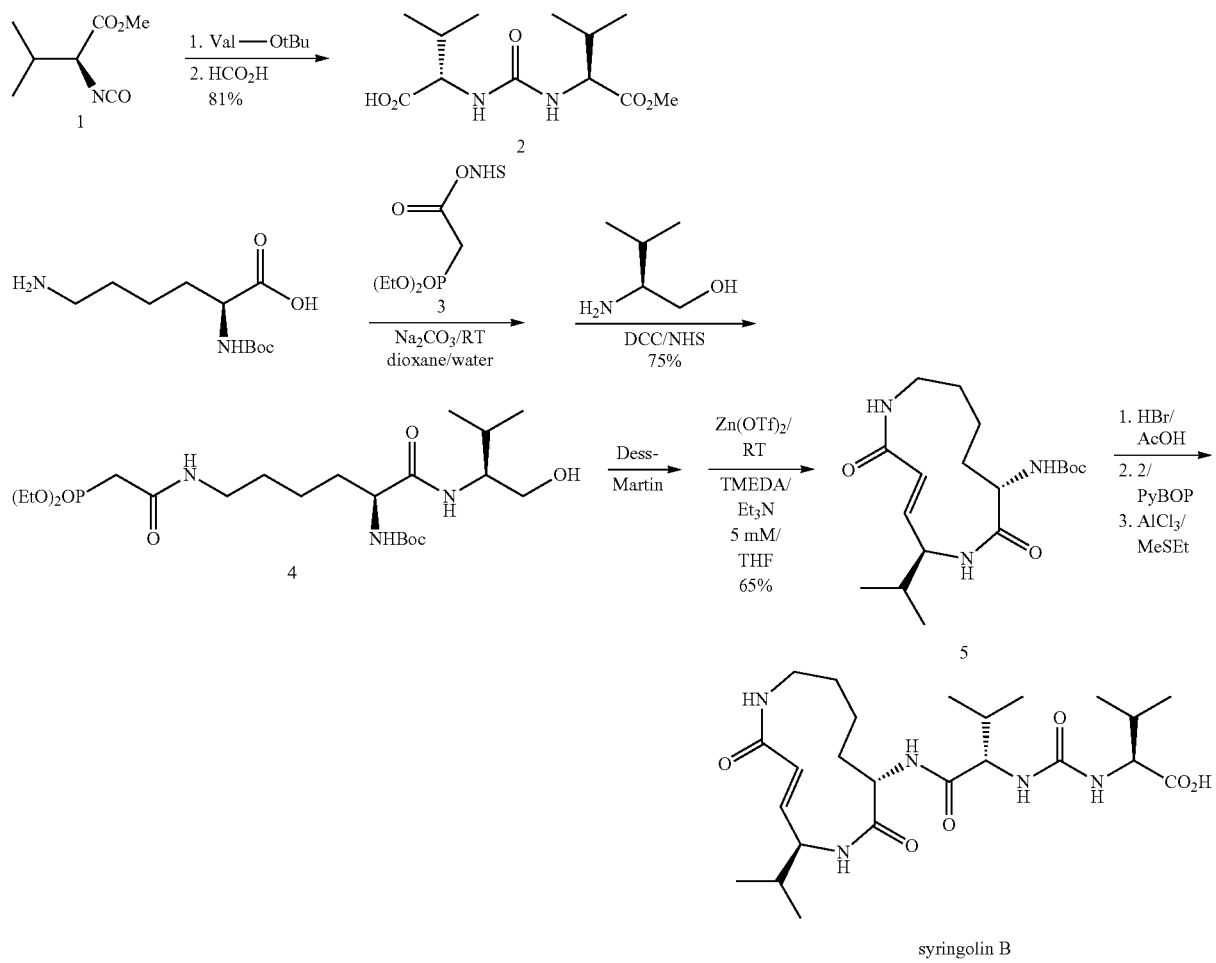

syringolin B

The disclosure provides methods for the synthesis of syrbactin and syrbactin derivatives and analogs. The disclosure provides core structures that may be further used in the generation of syrbactin derivatives using techniques known in the art.

Creation of the macrolactam poses the major challenge for the synthesis of the syringolins. Syringolin A was dissected into the bis-(valinyl)urea side chain and the 12-membered macrolactam core. The core was prepared with a protected diol as a synthon for the trans-α,β-unsaturated amide, and the formation of the macrolactam was achieved by ring-closing metathesis at about 49% yield. After side-chain attachment, the unsaturated amide was revealed. The syringolin B synthesis used lysine and valine as starting materials, assembled a polypeptide using standard coupling methods, and then The total synthesis of syringolin B demonstrates phosphonate macrocyclization techniques of the disclosure. The bis(valinyl)urea 2 required for the side-chain was prepared from the surprisingly commercially available L-valine-derived isocyanate 1 and L-valine tert-butyl ester. Boc-L-Lysine was acylated with the NHS active ester of diethylphosphonoacetic acid using a protocol developed for other acids, and then a conventional peptide coupling with L-valinol. The two-step yield of 4 is 75%. The Dess-Martin oxidation sets up the cyclization reaction. The very mild Horner-Wadsworth-Emmons protocol developed by Helquist for the formation of acrylamides with high E selectivity can be used. When applied at relatively high dilution using 2 eq $Zn^{++}$, 1 eq TMEDA, and 4 eq Et3N for 15 h, the cyclization product 5 is obtained in 75% yield. No stereoisomers (from poor stereoselectivity in the Horner-Wadsworth-Emmons reaction or epimerization of the intermediate α-aminoaldehyde) were detected in this product, nor dimers. The removal of the Boc group was performed with acid, and coupling with 2 used conventional peptide coupling reagents. A deprotection was used to give syringolin B. The resulting synthetic syringolin B sample gave spectroscopic properties ($^1$H NMR, $^{13}$C NMR, HRMS, IR) matching those reported for the natural product.

Scheme 2: Synthesis of Syringolin A

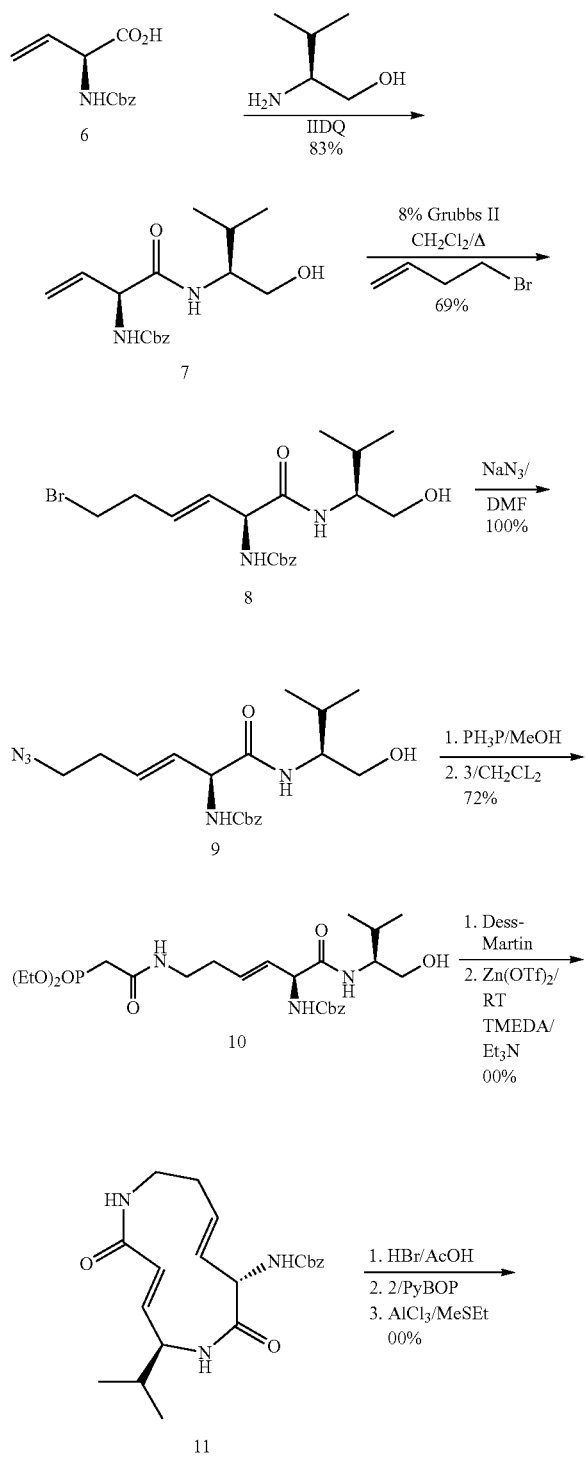

syringolin A

With the phosphonate macrocyclization proven in the syringolin B synthesis, synthesis of syringolin A was performed. A method to prepare 3,4-dehydrolysine intermediates, and the strategy that emerged to address this made this a more modular synthesis. Modules used for the macrolactam core include valinol and 3 from the first synthesis, vinyl glycine derivative 6, and 1-bromo-3-butene. Compound 6 is available in three steps from commercial Z -Met-OMe. Peptide coupling of vinyl glycine derivatives is known using conventional mixed anhydride protocols as well as the more exotic reagent IIDQ (2-isobutoxy-1-isobutoxycarbonyl-1,2-dihydroquinoline). The coupling of L-valinol with 6 gives 7 efficiently, though slowly, and without racemization. This step is significantly enhanced with microwave irradiation, wherein it can be complete in 10 min. One can take advantage of the commercial availability of 1-bromo-3-butene to use it in 10-fold excess in cross-metathesis with 7 using the Grubbs second-generation catalyst. This gives a product 8 that has exclusively the (E) stereochemistry. Nucleophilic substitution of 8 with azide introduces the last nitrogen. Staudinger reduction of the azide and then coupling with the phosphonoacetic acid active ester give 10 (72% for two steps). The oxidation and cyclization of this material (2 eq Zn$^{++}$, 1 eq TMEDA, 8 eq TEA, 2 mM, 12 h) are as successful as in the first synthesis. While the presence of two alkenes in the 12-membered ring are expected to increase the strain relative to syringolin B (calculated to be 13 kcal/mol by MMEF), this does not appear to be a significant impediments to the cyclization reaction. Again, no stereoisomers can be detected in product 11. This synthesis was completed by removal of the Cbz group with acid, peptide coupling of the side chain 2, and a final deprotection. The resulting synthetic syringolin A gave spectroscopic properties ($^1$H NMR, $^{13}$C NMR, HRMS, IR) matching those reported for the natural product and was identical by comparison to an authentic sample.

These syntheses proceed in 7 steps and 11 steps. They are modular and should permit the preparation of many structural variants that could improve on the biological properties of the parent natural products. They exploit a novel application of the Horner-Wadsworth-Emmons reaction that constructs a large lactam ring. This method using such reactions to make macrolactones is unexpected as amides have a greater preference for s-trans conformations that would disfavor cyclization, and 12-membered rings are not among the easier macrocycles to form. This feature adds chemical interest to the synthesis, as there are many other biologically active macrolactams that are accessible using this strategy. This route does not add any protecting groups, only removes those that were present in starting materials.

The disclosure provides a number of syrbactin analogs comprising a macrolactam core having general formulas I, II, and III and species of formulas 11-25. The disclosure provides compounds useful as starting materials to expand the diversity of syrbactins and accordingly, syrbactin analogs comprising such core structures are provided.

The disclosure provides syrbactin derivatives and a modular and general synthetic approach to the syringolins with the potential for straightforward preparation of structural variants by the substitution of structurally variant modules (diversity-oriented synthesis). The α,β-unsaturated amide of the syringolins suggested an intramolecular Horner-Wadsworth-Emmons condensation for the preparation of the 12-membered ring. Such reactions have found wide utility in the high-efficiency preparation of macrolactones.

The disclosure provides core compounds comprising general formula I, II or III:

Formula I

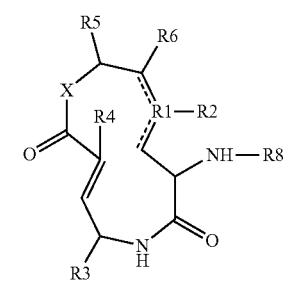

Formula II

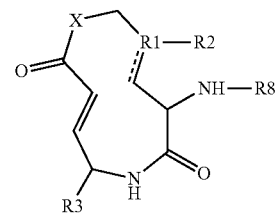

Formula III

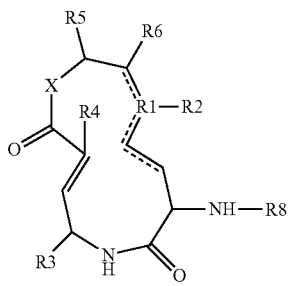

wherein $R_1$ is selected from O, S or C, wherein. $R_2$ is selected from O, H, aryl, substituted aryl, alkyl, substituted alkyl, carboxyl, aminocarbonyl, alkylsulfonylaminocarboxyl, alkoxycarbonyl, and halo, wherein $R_3$ is selected from H, $C(CH_3)_2$, aryl, substituted aryl, alkyl, substituted alkyl, carboxyl, aminocarbonyl, alkylsulfonylaminocarboxyl, alkoxycarbonyl, and halo, wherein $R_4$ is F or H, wherein $R_5$ and $R_6$ are independently H, $OR_7$, or $R_5$ and $R_6$, together with the carbons to which they are bound, can be joined to form a 4 to 7 membered ring or a substituted 4 to 7 membered ring, wherein $R_7$ is selected from H, aryl, substituted aryl, alkyl, substituted alkyl, carboxyl, aminocarbonyl, alkylsulfonylaminocarboxyl, alkoxycarbonyl, and halo, wherein $R_8$ H, an alkyl, a valinyl, or a bis(valinyl) and X is N or O. In one embodiment, $R_8$ comprises the structure:

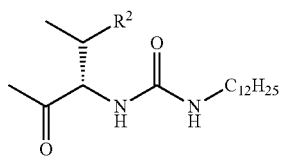

The application of these compounds in the syntheses provides a powerful and versatile method of generating diverse syrbactin. For example, a variety of commercial lysine analogs can be plugged directly into the syringolin B synthesis make variant cores. They are collected below as compounds 11-16. Comparing these compounds with intermediate 5 shows the structural diversity that is available. Note that core 14 is derived from the oxidation of core 12 (and that similar oxidations, to give the sulfoxide or sulfone, could be applied to 15). These cores can be acylated with a wide variety of acylating agents to give final products that have biological activity on the proteasome.

11

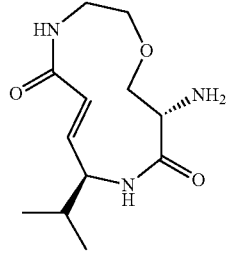

12

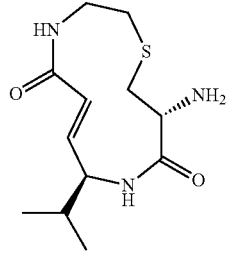

13

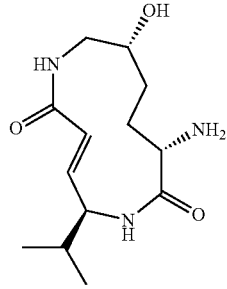

14

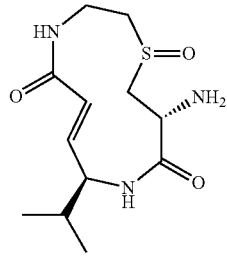

15

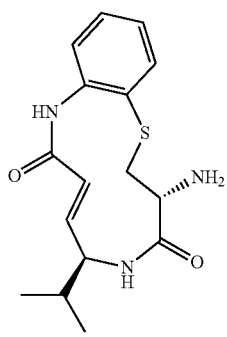

16

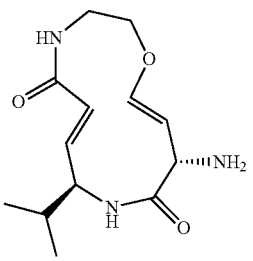

Variation of the starting materials used the syringolin A synthesis (see scheme II) permits an even greater variation in the core structure. The potential compounds are shown as 17-25 below. Use of another 1,2-aminoalcohol in place of valinol will give analogs such as 17, where the isopropyl group is replaced by any R group (alkyl or aryl, but not N, O, S, halide), while it might also be possible to use 1,3-aminoalcohols or 1,4-aminoalcohols. Substitution of a fluorinated phosphonic acid in the synthesis gives core analog 18, which exhibits modified reactivity with both its biological target molecule and off-target molecules. The unsaturated amide functional group is the site of the chemical reaction with the proteasome but may also react elsewhere. These two substitutions would also be possible in the syringolin B synthesis (see, scheme I) and with core analogs 11-16.

17

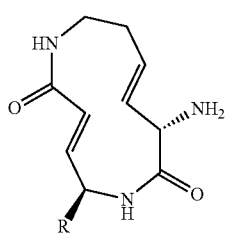

18

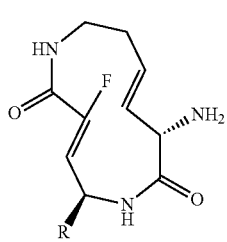

19

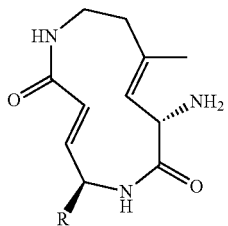

20

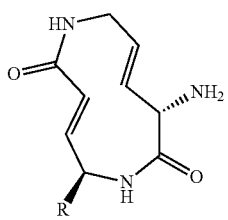

21

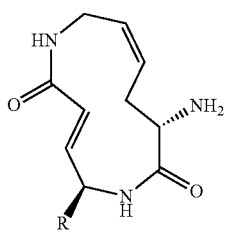

22

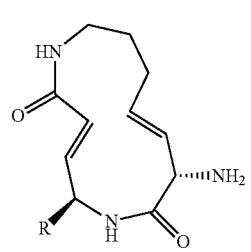

23

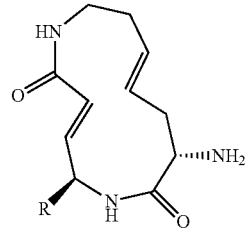

24

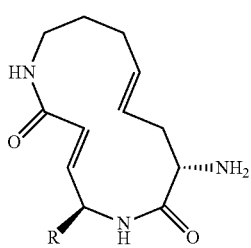

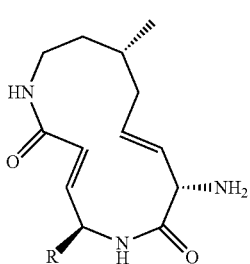

Alkyl groups can be added to the non-conjugated alkene (19), and the ring size and alkene position can be modified, all merely by using variants of the starting materials 6 and 1-bromo-3-butene. These variations lead to cores 20-24. Addition of alkyl or other groups to the ring, with specific stereochemistry, can be accomplished by incorporating those features into a 1-bromo-3-butene analog, and would result in molecules like 25.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. The term cyclopentyl ring refers to a ring of five carbons with any degree of unsaturation. The term cyclohexyl ring refers to a ring of six carbons with any degree of unsaturation.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted. Specified aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of R5 and R6 together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more CH$_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO2N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
—COOR where R is a hydrogen or an alkyl group or an aryl group and more specifically where R is methyl, ethyl, propyl, butyl, or phenyl groups all of which are optionally substituted:
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R═H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo -substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

Pharmaceutically acceptable salts comprise pharmaceutically-acceptable anions and/or cations. Pharmaceutically-acceptable cations include among others, alkali metal cations (e.g., Li+, Na+, K+), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl-, Br-), sulfate, acetates (e.g., acetate, trifluoroacetate), ascorbates, aspartates, benzoates, citrates, and lactate.

Compounds of the disclosure can have prodrug forms. Prodrugs of the compounds of the invention are useful in the methods of this disclosure. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 338-392).

Accordingly, the disclosure provides a plurality of syrbactin compounds comprising a core structure of Formula I, II, and III and more specific cores of Formula 11-25, As discussed above this disclosure provides novel compounds that have biological properties useful for the treatment of cancer and/or inflammatory disorders, and, in certain embodiments, more generally are useful as proteasome inhibitors. In certain embodiments, the compounds as useful for the treatment of cancer (including, but not limited to, prostate cancer, breast cancer, lung cancer, colon cancer, lymphoma, bladder cancer, cervical cancer, uterine cancer, melanoma and/or skin cancer, kidney cancer, testicular cancer, ovarian cancer, stomach cancer, leukemia, brain cancer, multiple myeloma, liver cancer, pancreatic cancer or esophageal cancer). In other embodiments, the compounds are useful for the treatment of inflammatory disorders, and/or disorders caused by activation of the regulatory subunits of the proteasome. These disorders include, but are not limited to inflammation, autoimmune diseases (e.g., rheumatoid arthritis, lupus erythematosus, multiple sclerosis), respiratory distress syndrome, neurological disease (e.g., Alzheimer's Disease), ischemia, cachexia, cystic fibrosis, neoplasm, and HIV infection.

Accordingly, in another aspect of the disclosure, pharmaceutical compositions are provided, which comprise any one of the compounds described herein (or a prodrug, pharmaceutically acceptable salt or other pharmaceutically acceptable derivative thereof, and optionally comprise a pharmaceutically acceptable carrier. In certain embodiments, these compositions optionally further comprise one or more additional therapeutic agents. Alternatively, a compound of this disclosure may be administered to a patient in need thereof in combination with the administration of one or more other therapeutic agents. For example, additional therapeutic agents for conjoint administration or inclusion in a pharmaceutical composition with a compound of this disclosure may be an anti-inflammatory agent (e.g., an agent for the treatment of rheumatoid arthritis or psoriasis) or cytotoxic agent or anticancer agent approved for the treatment of cancer, as discussed in more detail herein, or it may be any one of a number of agents undergoing approval in the Food and Drug Administration that ultimately obtain approval for the treatment of cancer or an inflammatory disorder. It will also be appreciated that certain of the compounds of disclosure can exist in free form for treatment, or where appropriate, as a pharmaceutically acceptable derivative thereof. According to the disclosure, a pharmaceutically acceptable derivative includes, but is not limited to, pharmaceutically acceptable salts, esters, salts of such esters, or a prodrug or other adduct or derivative of a compound of this disclosure which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the disclosure, or separately by reacting a free base or free acid function with a suitable reagent, as described generally below. For example, a free base function can be reacted with a suitable acid. Furthermore, where the compounds of the disclosure carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonte, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present disclosure which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the disclosure. The term "prodrug" refers' to compounds that are rapidly transformed in vivo to yield the parent compound of any of the above formulas, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the disclosure additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the Judgment of the formulator.

As described in more detail herein, in general the disclosure provides compounds that comprise a core structure of Formula I, II or III that may be used or further derivatized to generate syrbactins useful for the treatment of cancer and inflammatory disorders. Without wishing to be bound by any particular theory, more generally, the compounds of the disclosure have also been shown to act as proteasome inhibitors and thus may be useful more generally for a variety of disorders that are affected by processes regulated by the proteasome (e.g., cell cycle, activation of NFkB, to name a few).

As discussed above, compounds of the disclosure can have antiproliferative and antitumor activity. As such, compounds of the disclosure are particularly useful for the treatment of cancer, and in certain embodiments for the treatment of solid tumors. Additionally, the compounds are useful as proteasome inhibitors and can thus be used for the treatment of a variety of disorders, as discussed herein that are affected by the proteasome.

Thus, as described above, in another aspect of the disclosure, a method for the treatment of cancer is provided comprising administering a therapeutically effective amount of a compound comprising a core ring structure of Formula I, II or III or of any one of formula 11-25, as described herein, to a subject in need thereof. It will be appreciated that the compounds and compositions, according to the method of the present disclosure, may be further derivatized and may be administered using any amount and any route of administration effective for the treatment of cancer. Thus, the expression "effective amount" as used herein, refers to a sufficient amount of agent to kill or inhibit the growth of tumor cells. In other embodiments, compounds may be useful for the treatment of inflammatory disorders, or other disorders affected by proteasome inhibition and thus "effective amount" refers to a sufficient amount of agent to treat or ameliorate the symptoms of the inflammatory disorder, or alternatively, refers to a sufficient amount to effect proteasome inhibition. The exact amount required will vary from subject to subject, depending on the species, age, and general condition of the subject, the severity of the infection, the particular therapeutic agent, its mode of administration, and the like. The compounds of the disclosure are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present disclosure will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this disclosure can be administered to humans and other animals orally, rectally, parenterally, intracisternally, intravaginally, intraperitoneally, topically (as by powders, ointments, or drops), bucally, as an oral or nasal spray, as an aerosol, or the like, depending on the severity of the infection being treated. In certain embodiments, the compounds of the disclosure may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolic and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this disclosure include ointments, pastes, creams, lotions, gels, powders, solutions, sprays, aerosols, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the disclosure can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. For example, other therapies or anticancer agents that may be used in combination with the inventive anticancer agents of the present disclosure include surgery, radiotherapy (in but a few examples, .gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http:~~www.nci.nih.gov/, a list of the FDA approved oncology drugs at http:~~www.fda.gov/cder/cancer/druglistframe.htm, and The Merck Manual, Seventeenth Ed. 1999, the entire contents of which are hereby incorporated by reference. It will also be appreciated that the therapies employed may achieve a desired effect for the same disorder (for example, a compound may be administered concurrently with another anti-inflammatory agent or anticancer agent), or they may achieve different effects (e.g., control of any adverse effects).

In certain embodiments, the pharmaceutical compositions of the disclosure further comprise one or more additional therapeutically active ingredients (e.g., chemotherapeutic and/or palliative). For purposes of the disclosure, the term "Palliative" refers to treatment that is focused on the relief of symptoms of a disease and/or side effects of a therapeutic regimen, but is not curative. For example, palliative treatment encompasses painkillers, antinausea medications and antisickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

In other embodiments, the disclosure relates to a kit for conveniently and effectively carrying out the methods in accordance with the disclosure. In general, the pharmaceutical pack or kit comprises one or more containers filled with one or more of the ingredients of the pharmaceutical compositions of the disclosure. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The compounds comprising core structures of the disclosure may be screened for activity by using common methods without undue experimentation. For example, to examine the effect of syrbactin derivatives comprising a core of general formula I, II or II on the proliferation rate of mammalian cancer cells, the derivative was synthesized as described above and purified. The purity of the syrbactin derivative is confirmed by reverse-phase HPLC using a standard. Lyophilized syrbactin derivatives is dissolved in ultra-pure distilled water (Invitrogen, Carlsbad, Calif.) at a concentration of 2.5 mM (stock solution), sterile-filtered with a 0.2 micron filter, aliquoted into sterile tubes and stored frozen at −80 C. Aliquots are thawed and used for cell culture studies at different concentrations as indicated below.

The mammalian cell lines used to test the effects of syringolin A is human neuroblastoma (NB) cells with either wild type p53 (line SK-N-SH, provided by the American Type Culture Collection [ATCC], Manassas, Va.; Davidoff, et al. 1992. Oncogene 7:127-133; McKenzie, et al. 1999. Clin. Cancer Res. 5:4199-4207; Tweddle, et al. 2001. Am. J. Pathol. 158:2067-2077), mutant p53(line LAN-1, cysteine to stop codon at residue 182; Davidoff, et al. 1992. Oncogene 7:127-133; Tweddle, et al. 2001. Cancer Res. 61:8-13; Tweddle, et al. 2003. Cancer Lett. 197:93-98), or human ovarian cancer cells (line SKOV3, Cancer Research Center of Hawaii). NB cells are maintained in RPMI 1640 (Biosource, Rockville, Md.) containing 10% (v/v) heat-inactivated fetal bovine serum (FBS) (Invitrogen, Carlsbad, Calif.), penicillin (100 IU/ml), and streptomycin (100 ug/ml) as previously described (Wallick, et al, 2005. Oncogene 24:5606-5618). SKOV3 cells are maintained in McCoy's 5A with L-glutamine (Mediatech Inc., Herndon, Va.) and containing 10% (v/v) heat-inactivated fetal bovine serum (PBS) (Invitrogen, Carlsbad, Calif.) and gentamicin (100 uL/mL). Cells are seeded 18-24 hours before syrbactin derivative treatment and analyzed after 24 and/or 48 hours. Cell numbers are determined using a haemacytometer in the presence of trypan blue (Fisher Scientific, Pittsburgh, Pa.).

To test the effects of the syrbactin derivatives on proliferation, cells at $0.25\text{-}0.5\times10^5$ cells per ml are seeded in 96-well microtiter plates containing 100 ul of culture medium per well. After 24 hours, a syrbactin derivative is added to wells to a final concentration of 0.5 um to 100 um. Cells are incubated for 48 hours, photographed, and the viability of cells (calculated as a percentage of control cell counts) is determined using the sulphorhodamine B (SRB) assay as previously reported (Skehan, et al. 1990. J. Natl. Cancer Inst. 82:1107-1112, which is incorporated herein by reference in its entirety). In brief, cell culture medium was removed from the microtiter plate and adherent cells were fixed with 10% (w/v) trichloracetic acid (TCA) for 30 minutes at room temperature. Following four washes with tap water, 100 ul of SRB (Sigma Chemical Co., St. Louis, Mo.) (0.4 g/100 ml 1% [v/v] glacial acetic acid in water) is added and the plate is then incubated for 30 minutes at room temperature, and rinsed four times with 3% (v/v) glacial acetic acid. After addition of 200 µl of 10 mM Iris base (not pH adjusted) to each well, the plate is incubated on an orbital shaker for 30 minutes until the SRB is uniformly dissolved. The absorption at a wavelength of 560 nm is read using an HTS 7000 Plus Bioassay Reader or a Victor 3, 1420 Multilabel Counter (PerkinElmer, Inc. Boston, Mass.). To record cell morphology with and without syrbactin treatment, photomicrographs are taken of cells in 12-well plates or 96-well plates, in the presence or absence of 25 uM syrbactin, using a Nikon Diaphot inverted microscope (Nikon Corp., Tokyo, Japan) and a Carl Zeiss Axiovert 200M inverted microscope (Carl Zeiss, Goettingen, Germany), both equipped with a digital camera and computer software for image processing. Power of magnification for SK-N-SH, LAN-1, and SKOV3 cells can he done at 20×, and for Rat-1 cells at 10×.

The following example is meant to illustrate, but not limit, the broader invention described herein.

Examples

The compounds described below can be identified using the following table:

TIR 26

| | $R^1$ | $R^2$ | X | Z |
|---|---|---|---|---|
| a: | iPr | Me | NH | ($CH_2CH_2$) |
| b: | iPr | Et | NH | ($CH_2CH_2$) |
| c: | iPr | Me | O | (CH=CH) |
| d: | Me | Me | NH | ($CH_2CH_2$)(TIR48) |

Biological Activity of Novel, Syrbactin-Based Proteasome Inhibitors:

Experiments were performed to examine the biological activity of syrbactin analogs that were designed and synthesized as described herein. First an in vitro toxicity of two first-generation syrbactin analogs, called TIR-24 and TIR-42, was performed using a conventional MTT assays that measure cell survival after 48 hours of drug treatment. The human REH acute lymphocytic leukemia cell line was used. Both compounds were moderately cytotoxic with an $IC_{50}$ of about 100 µM for TIR-24 and approximately 30 µM for TIR-42. Subsequent modifications of these agents increased their biological activity dramatically, and representative examples are shown in FIG. 1. Second-generation syrbactin analogs, such as TIR-26 and TIR-48 displayed cytotoxic activity in MTT assays with $IC_{50}$s in the range of 50-100 nM, which represented an improvement of nearly two orders of magnitude. Although this impressive level of potency already may very well be within the range of (future) clinical efficacy, designing additional streamlined analogs with further improved activity can be performed based upon the core structures of the disclosure.

Bortezomib (BZM), the first proteasome inhibitor to reach the clinic, is being used to treat patients with multiple myeloma and mantle cell lymphoma, and this is reflective of this agent's differential potency in different tumor cell types. FIG. 2, left panel, shows, for example, that BZM is more cytotoxic to multiple myeloma cells (in this case: the RPMI/8226 cell line) than to acute lymphocytic leukemia cells (in this case: the REH cell line). In comparison, the right panel of FIG. 2 demonstrates that TIR-48 is equally effective in both cell lines, which bodes well with respect to future clinical applications for different hematologic malignancies.

FIG. 3 shows Western blot analysis of REH cells treated with increasing concentrations of TIR-48, and as a positive control, with BZM. An antibody against ubiquitin to reveal the presence of ubiquitinated proteins, which accumulate (and present as a smear, due to different molecular weights) in response to the inhibition of proteasome activity. Actin was used as a loading control. FIG. 3 reveals substantial accumulation of ubiquitinated proteins during TIR-48 (and BZM) treatment, and thus confirms the proteasome inhibitory potency of these compounds.

In order to obtain preliminary insight into the molecular events triggered by TIR-48, several intracellular targets that were known to be relevant for the cytotoxic effects of BZM were investigated. REH leukemia cells were treated with increasing concentrations of TIR-48, or with BZM, or with solvent (solv.) alone, and cellular lysates were analyzed by Western blot. FIG. 3 indicates that TIR-48 does not appear to mimic all of the effects of BZM, which suggests differential consequences of proteasome inhibition (which might be possible due to the recognized differential mechanism by which syrbactins inhibit proteasome activity, as compared to BZM)—or it may indicate additional molecular targets of these compounds. PARP cleavage indicates ongoing apoptosis, which appears to have different kinetics in TIR-48 vs. BZM. Mcl-1, an anti-apoptotic protein that protects cells from chemotherapy, is more effectively down-regulated by TIR-48, which represents a beneficial feature. Both CHOP and ATF3, important ER stress regulators, are more strongly induced by TIR-48, which is beneficial as well, because it indicates more severe ER stress that can be further exploited for therapy. Similar results were obtained with other cell lines representing lymphoma, leukemia, multiple myeloma, and Waldenström's macroglobulinemia.

Altogether, these results provide proof that the syrbactin derivatives comprising the various core structures disclosed herein greatly increase proteasome inhibitory potency of syrbactins, and that such analogs display very promising cytotoxic features in various cell lines derived from different types of hematologic tumors, including childhood leukemia.

Various embodiments have been described, other embodiments will be readily apparent to one of skill in the art.

What is claimed is:

1. A method to synthesize a compound 1 having the structure of:

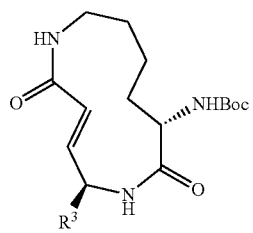

1 comprising reactions (a)-(d):

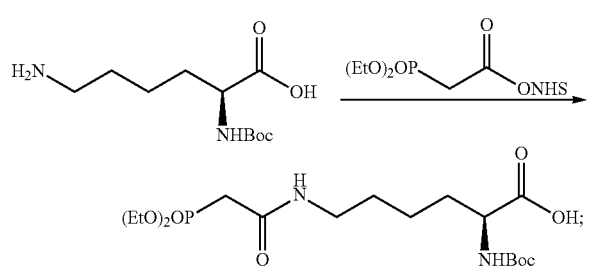

(a)

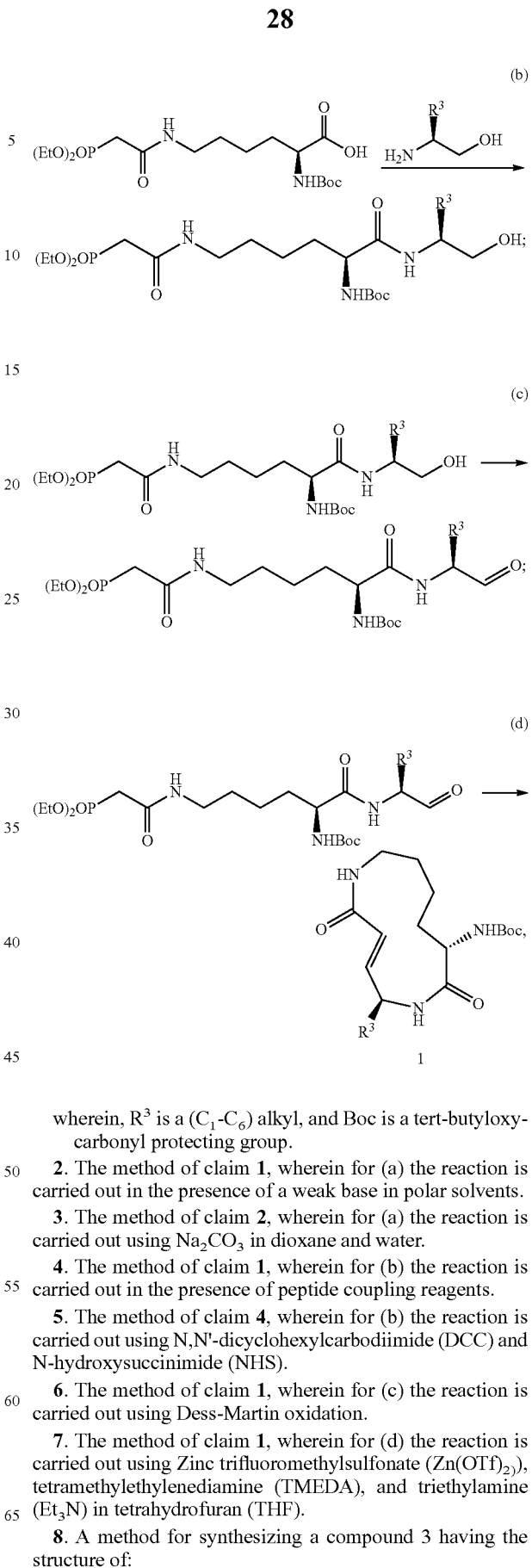

wherein, $R^3$ is a ($C_1$-$C_6$) alkyl, and Boc is a tert-butyloxycarbonyl protecting group.

2. The method of claim 1, wherein for (a) the reaction is carried out in the presence of a weak base in polar solvents.

3. The method of claim 2, wherein for (a) the reaction is carried out using $Na_2CO_3$ in dioxane and water.

4. The method of claim 1, wherein for (b) the reaction is carried out in the presence of peptide coupling reagents.

5. The method of claim 4, wherein for (b) the reaction is carried out using N,N'-dicyclohexylcarbodiimide (DCC) and N-hydroxysuccinimide (NHS).

6. The method of claim 1, wherein for (c) the reaction is carried out using Dess-Martin oxidation.

7. The method of claim 1, wherein for (d) the reaction is carried out using Zinc trifluoromethylsulfonate ($Zn(OTf)_2$), tetramethylethylenediamine (TMEDA), and triethylamine ($Et_3N$) in tetrahydrofuran (THF).

8. A method for synthesizing a compound 3 having the structure of:

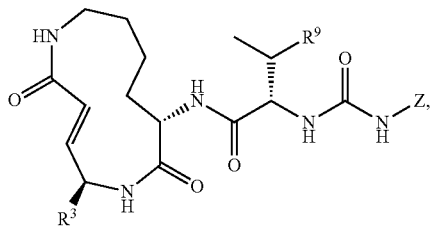

3 comprising reactions (a)-(d) of claim 1, and further comprising reaction (e):

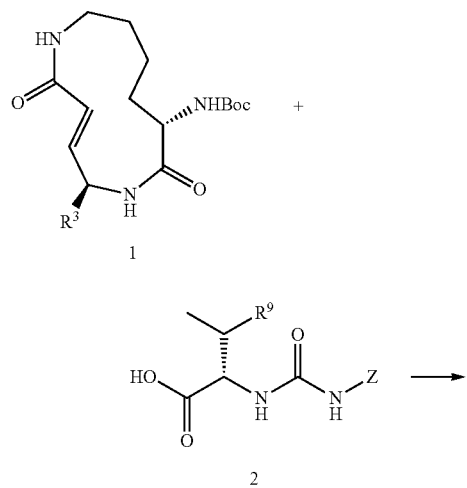

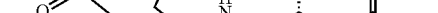

(e)

wherein, $R^9$ is either a methyl or an ethyl, and z is an unsubstituted ($C_{11}$-$C_{16}$) alkyl.

9. The method of claim 8, wherein for reaction (e), the Boc group of 1 is removed by treating with hydrobromic acid in acetic acid.

10. The method of claim 9, wherein de-protected 1 is coupled with 2 using a peptide coupling reagent.

11. The method of claim 10, wherein the peptide coupling reagent is benzotriazol-1-yl-oxytripyrrolidinophosphonium hexafluorophosphate (PyBOP).

12. The method of claim 7, wherein compound 3 has the structure of:

* * * * *